United States Patent [19]
Bedingham

[11] Patent Number: 5,984,892
[45] Date of Patent: *Nov. 16, 1999

[54] BLOOD ASPIRATOR

[75] Inventor: William Bedingham, Woodbury, Minn.

[73] Assignee: Minnesota Mining and Manufacturing Company, St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/714,354

[22] Filed: Sep. 16, 1996

[51] Int. Cl.$^6$ ........................................... A61M 1/00
[52] U.S. Cl. ........................................ 604/67; 128/DIG. 13
[58] Field of Search ................... 604/30, 31, 49, 604/50, 52, 53, 65–67, 207; 128/DIG. 12, DIG. 13

[56] References Cited

U.S. PATENT DOCUMENTS

| | | |
|---|---|---|
| 478,872 | 7/1892 | Kirkwood . |
| 1,114,268 | 10/1914 | Kells . |
| 2,804,075 | 8/1957 | Borden ................... 128/277 |
| 3,191,600 | 6/1965 | Everett ................... 128/276 |
| 3,412,510 | 11/1968 | Harcuba .................... 52/127 |
| 3,542,031 | 11/1970 | Taylor ..................... 128/304 |
| 3,623,483 | 11/1971 | Dyer, Jr. .................. 128/276 |
| 3,680,560 | 8/1972 | Pannier, Jr. et al. ........ 128/276 |
| 3,685,517 | 8/1972 | Reynolds et al. ........... 128/277 |
| 3,704,709 | 12/1972 | Sorenson et al. ........... 128/277 |
| 3,799,702 | 3/1974 | Weishaar .................... 417/38 |
| 3,849,071 | 11/1974 | Kayser .................... 23/258.5 |
| 3,863,634 | 2/1975 | Reynolds et al. ........... 128/276 |
| 3,866,608 | 2/1975 | Reynolds et al. ........... 128/276 |
| 3,929,126 | 12/1975 | Corsaut .................... 128/240 |
| 3,955,573 | 5/1976 | Hansen et al. ............. 128/276 |
| 3,958,573 | 5/1976 | Wiley ..................... 128/276 |
| 3,964,484 | 6/1976 | Reynolds et al. ........... 128/276 |
| 3,965,896 | 6/1976 | Swank ................... 128/214 R |
| 3,993,067 | 11/1976 | Schachet et al. .......... 128/214 C |
| 4,002,170 | 1/1977 | Hansen et al. ............. 128/276 |

(List continued on next page.)

FOREIGN PATENT DOCUMENTS

| | | |
|---|---|---|
| 0 158 037 | 10/1985 | European Pat. Off. ......... A61M 1/00 |
| 2 371 202 | 6/1978 | France ..................... A61M 1/03 |
| 33 21 4 | 5/1983 | Germany . |
| 195 02 305 | 8/1996 | Germany ................. A61F 9/007 |
| WO 94/03098 | 2/1994 | WIPO . |
| WO 98/21094 | 5/1998 | WIPO . |

OTHER PUBLICATIONS

"Autotransfusion Reference Materials", *Electromedics*, Inc., 6 pages.

William Bell, M.D., "The Hematology of autotransfusion", *Surgery*, vol. 84, No. 5, Nov. 1978, pp. 695–699.

A. Robert Cordell, M.D. et al., "An Appraisal of Blood Salvage Techniques in Vascular and Cardiac Operations", *The Annals of Thoracic Surgery*, vol. 31, No. 5, May 1981, pp. 421–425.

*Primary Examiner*—Michael Buiz
*Assistant Examiner*—Manuel Mendez
*Attorney, Agent, or Firm*—Robert W. Sprague; Stephen W. Bauer; Martin J. Hirsch

[57] ABSTRACT

A blood aspirator is composed of a suction circuit adapted to receive a flow of blood, a sensor associated with the suction circuit for generating a signal relating to the presence of bubbles in aspirated blood in the suction circuit, a variable speed pump coupled to the suction circuit and adapted to pump blood through the suction circuit, and a controller for controlling the speed of the pump. The controller causes the pump to adjust the blood flow through the suction circuit so that a predetermined, nonzero concentration of bubbles flows through the suction circuit.

20 Claims, 6 Drawing Sheets

U.S. PATENT DOCUMENTS

| | | | |
|---|---|---|---|
| 4,004,590 | 1/1977 | Muriot | 128/276 |
| 4,006,745 | 2/1977 | Sorenson et al. | 128/214 R |
| 4,014,329 | 3/1977 | Welch et al. | 128/214 R |
| 4,047,526 | 9/1977 | Reynolds et al. | 128/214 R |
| 4,068,664 | 1/1978 | Sharp et al. | 128/276 |
| 4,082,959 | 4/1978 | Nakashima | 250/577 |
| 4,156,149 | 5/1979 | Vaccari | 250/577 |
| 4,191,182 | 3/1980 | Popovich et al. | 128/214 R |
| 4,205,677 | 6/1980 | Engstrom | 128/276 |
| 4,274,705 | 6/1981 | Miller | 350/96.15 |
| 4,299,705 | 11/1981 | Russell | 210/647 |
| 4,321,921 | 3/1982 | Laszczower | 128/276 |
| 4,368,118 | 1/1983 | Siposs | 210/136 |
| 4,411,786 | 10/1983 | Russell | 210/321.3 |
| 4,424,053 | 1/1984 | Kurtz et al. | 604/4 |
| 4,430,084 | 2/1984 | Deaton | 604/317 |
| 4,435,170 | 3/1984 | Laszczower | 604/4 |
| 4,443,220 | 4/1984 | Hauer et al. | 604/408 |
| 4,466,888 | 8/1984 | Verkaart | 210/232 |
| 4,468,567 | 8/1984 | Sasano et al. | 250/577 |
| 4,487,600 | 12/1984 | Brownlie et al. | 604/35 |
| 4,493,706 | 1/1985 | Gordon et al. | 604/122 |
| 4,500,308 | 2/1985 | Kurtz et al. | 604/4 |
| 4,540,406 | 9/1985 | Miles | 604/269 |
| 4,547,186 | 10/1985 | Bartlett | 604/4 |
| 4,631,050 | 12/1986 | Reed et al. | 604/4 |
| 4,643,713 | 2/1987 | Viitala | 604/4 |
| 4,692,140 | 9/1987 | Olson | 604/40 |
| 4,708,714 | 11/1987 | Larsson et al. | 604/5 |
| 4,715,848 | 12/1987 | Beroza | 604/35 |
| 4,736,748 | 4/1988 | Nakamura et al. | 128/632 |
| 4,772,256 | 9/1988 | Lane et al. | 604/4 |
| 4,796,644 | 1/1989 | Polaschegg | 128/760 |
| 4,828,543 | 5/1989 | Weiss et al. | 604/4 |
| 4,838,865 | 6/1989 | Flank et al. | 604/118 |
| 4,850,995 | 7/1989 | Tie et al. | 604/6 |
| 4,850,998 | 7/1989 | Schoendorfer | 604/28 |
| 4,886,487 | 12/1989 | Solem et al. | 604/5 |
| 4,906,845 | 3/1990 | Bellhouse et al. | 250/227.28 |
| 4,976,682 | 12/1990 | Lane et al. | 604/4 |
| 4,988,336 | 1/1991 | Kohn | 604/67 |
| 4,994,682 | 2/1991 | Woodside | 250/577 |
| 5,005,005 | 4/1991 | Brossia et al. | 340/604 |
| 5,035,865 | 7/1991 | Inaba et al. | 422/99 |
| 5,087,250 | 2/1992 | Lichte et al. | 604/321 |
| 5,242,404 | 9/1993 | Conley et al. | 604/119 |
| 5,325,850 | 7/1994 | Ulrich et al. | 128/200.26 |
| 5,380,280 | 1/1995 | Peterson | 604/65 |
| 5,411,472 | 5/1995 | Steg, Jr. et al. | 604/4 |
| 5,419,768 | 5/1995 | Kayser | 604/119 |
| 5,441,482 | 8/1995 | Clague et al. | 604/35 |

OTHER PUBLICATIONS

*The New England Journal of Medicine*, p. 1276, 1 page.

Robert G. Johnson, M.D. et al., "The Efficacy of Postoperative Autotransfusion in Patients Undergoing Cardiac Operation", *The Annals of Thoracic Surgery*, vol. 36, No. 2, Aug. 1983, pp. 173–179.

Pleur–EVAC Autotransfusion system brochure, Deknatel Division, 6 pages, 1986.

Hartzell V. Schaff, M.D. et al., "Routine Use of Autotransfusion Following Cardiac Surgery: Experience in 700 Patients", *The Annals of Thoracic Surgery*, vol. 27, No. 6, Jun. 1979, pp. 493–499.

Robert L. Thurer, M.D. et al., "Autotransfusion Following Cardiac Operations: A Randomized, Prospective Study", *The Annals of Thoracic Surgery*, vol. 27, No. 6, Jun. 1979, pp. 500–507.

L. Dieter Voegele, M.D. et al., "An Improved Method for Collection of Shed Mediastinal Blood for Autotransfusion", 1981 by *The Society of Thoracic Surgeons*, 2 pages.

"Autologous Blood Transfusions", *Journal of the American Medical Association*, Nov. 7, 1986, Vol. 256, No. 17, pp. 2378–2380.

Cynthia T. Clague, Ph.D. et al., "A Low–Hemolysis Blood Aspirator Conserves Blood During Surgery", *Biomedical Instrumentation & Technology*, Sep./Oct. 1995, pp. 419–424.

G. Wright et al., "Cellular aggregation and trauma in cardiotomy suction systems", *Thorax*, 1979, pp. 621–628.

P. W. Boonstra, M.D. et al., "Reduced platelet activation and improved hemostasis after controlled cardiotomy suction during clinical membrane oxygenator perfusions", *The Journal of Thoracic and Cardiovascular Surgery*, vol. 89, No. 6, Jun. 1985, pp. 900–906.

Teruo Hirose, M.D. et al., "Reduction Of Perfusion Hemolysis By The Use Of Atraumatic Low–Pressure Suction", *The Journal of Thoracic and Cardiovascular Surgery*, vol. 47, No. 2, Feb. 1964, pp. 242–247.

J. C. F. de Jong, M.Sc. et al., "Hematologic aspects of cardiotomy suction in cardiac operations", *The Journal of Thoracic and Cardiovascular Surgery*, vol. 79, No. 2, Feb. 1980, pp. 227–236.

*ECRI Technology for Perfusion*, "Automated Intraoperative processing Autotransfusion Machines", vol. 1, No. 4, Nov. 1988, 5 pages.

Cynthia T. Clague et al., "An Atraumatic Aspirator for Use in Autologous Transfusion and Cardiac Bypass", 6 pages.

Dyer, Jr., M.D. et al., "Atraumatic Aspiration of Whole Blood for Intraoperative Autotransfusion", *The American Journal of Surgery*, vol. 123, May 1972, pp. 510–514.

H. J. ten Duis, et al., "Improved Hemocompatibility In Open Heart Surgery", *Trans. Am. Soc. Artif. Intern. Organs*, vol. XXIV, 1978, pp. 656–661.

Copy of message regarding Harvest Technologies sent to the inventor of the above application on or about Apr. 30, 1996 (with portions redacted).

FIG. 3
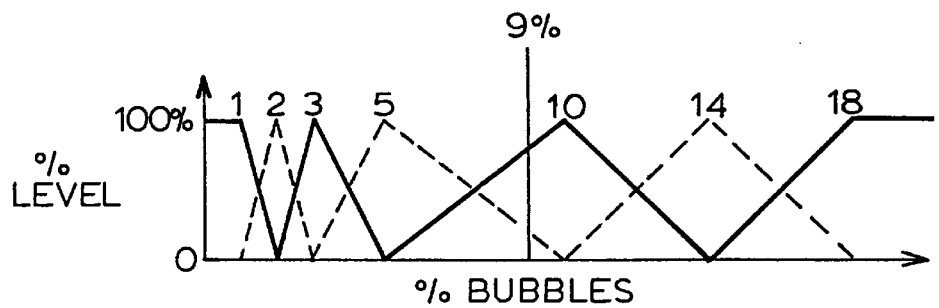
FIG. 4
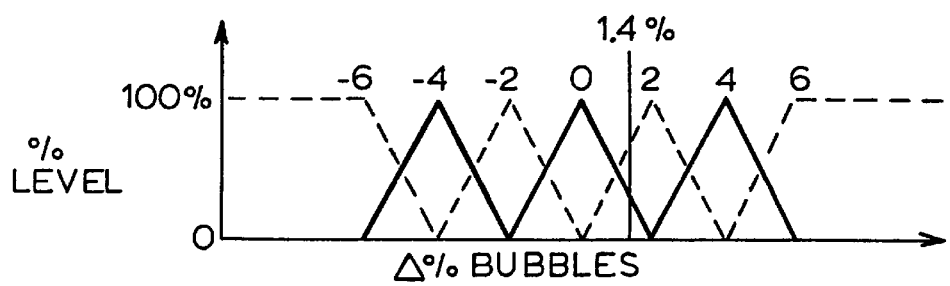
FIG. 5

BLOOD ASPIRATOR

BACKGROUND OF THE INVENTION

The present invention is directed to a blood aspirator that reduces the intake of air bubbles during aspiration of blood to reduce damage to the aspirated blood due to aspiration of the bubbles.

Vacuum-operated blood aspirators are conventional devices which are used in certain cases to remove blood from a patient, such as during a surgical procedure. The removed blood may be reinfused back into the patient at substantially the same time as it is removed to eliminate the need to obtain blood from an alternative blood source. Although re-use of vacuum-aspirated blood is generally advantageous, it has been recognized that aspiration may damage the blood due to air bubbles entrained in the aspirated blood. For example, in an article entitled "A Low-Hemolysis Blood Aspirator Conserves Blood During Surgery," Clague, et al. state that "Blood damage caused by traditional vacuum-operated suction tubes, particularly when air is aspirated along with the blood, usually exceeds damage from all other components. In addition to platelet injury, there is a high degree of hemolysis, which leads to high plasma hemoglobin levels and reduces the number of red blood cells available for reinfusion during cases of blood conservation, such as autologous transfusion and cardiac bypass."

U.S. Pat. No. 4,976,682 to Lane, et al. discloses a blood recovery system that reduces blood damage by minimizing the intake of air bubbles in the aspirated blood. The Lane, et al. blood recovery system includes a suction pump for aspirating blood and a bubble detector for detecting the presence of bubbles in the aspirated blood. As described in column 13, lines 34–42 of the Lane, et al. patent, as soon as a bubble is detected within the suction tip at the bubble detector, the speed of the suction pump is reduced. The pump speed continues to be reduced until no air is detected by the bubble detector. When the vacuum pump slows to the point where no air is detected by the bubble detector, the suction pump speeds up slightly until a small bubble appears at the suction tip, at which time the pump again slows.

SUMMARY OF THE INVENTION

The invention is directed to a blood aspirator having a suction circuit adapted to receive a flow of blood, sensor means associated with the suction circuit for generating a signal relating to the presence of bubbles in aspirated blood in the suction circuit, a variable speed pump coupled to the suction circuit and adapted to pump blood through the suction circuit, and control means for controlling the speed of the pump. The control means may include means for causing the pump to increase blood flow through the suction circuit when bubbles are present in the aspirated blood and/or means for causing the pump to adjust the blood flow through the suction circuit so that a predetermined, nonzero concentration of bubbles flows through the suction circuit.

The control means may also include means for causing the pump to increase the blood flow through the suction circuit in response to a bubble concentration that is lower than a predetermined nonzero value and means for causing the pump to decrease the blood flow through the suction circuit in response to a bubble concentration that is higher than a predetermined nonzero value. The control means may control the pump based upon the bubble concentration and a flow signal relating to the magnitude of blood flow through the suction circuit, and the control means may also control the pump based on the rate of change over time of the bubble concentration.

The blood aspirator may include memory means for storing a plurality of bubble concentration ranges, each of the ranges having an associated factor relating to the pump speed, means for determining which of the bubble concentration ranges the bubble concentration falls within, and means for controlling the pump speed based upon the factor associated with the bubble concentration determined by the determining means.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 3 illustrates a memory table in which a plurality of speed factors are stored;

FIG. 4 illustrates a graph relating to the concentration of bubbles detected by the sensor of FIG. 1;

FIG. 5 illustrates a graph relating to the change in concentration of the bubbles detected by the sensor of FIG. 1.

DETAILED DESCRIPTION OF THE PREFERRED EMBODIMENTS

Figure 1:
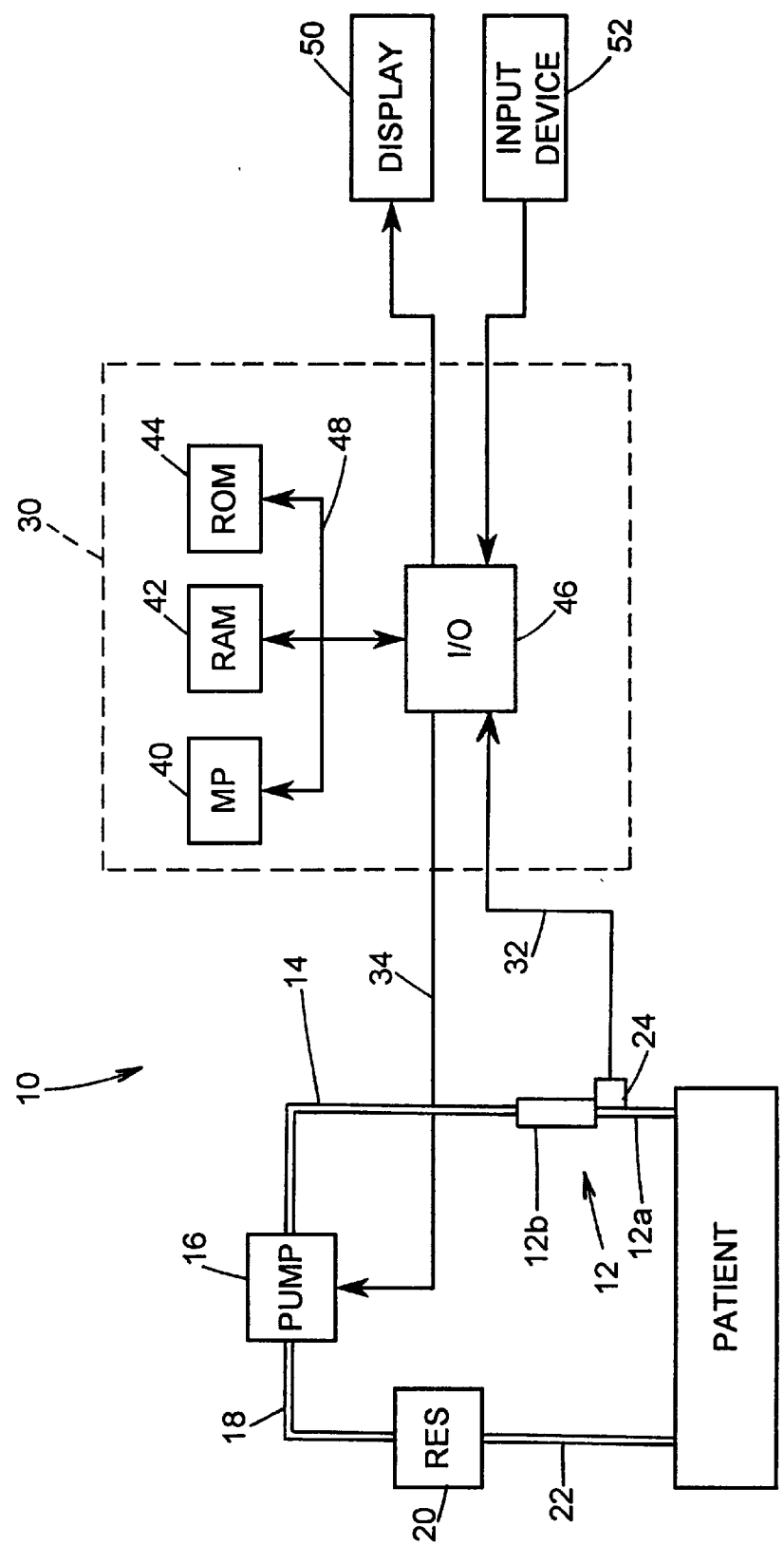
FIG. 1 is a block diagram of a preferred embodiment of a blood aspirator in accordance with the invention which is shown connected to a patient.

FIG. 1 illustrates a preferred embodiment of a blood aspirator 10 in accordance with the invention which may be used to evacuate blood from a surgical area during surgery, for example. The blood aspirator 10 includes a blood suction circuit composed of a suction device 12, a liquid conduit 14 connected to the suction device 12, a variable speed pump 16 connected to the liquid conduit 14, a second liquid conduit 18 connected to the pump 16, a blood reservoir 20 connected to the conduit 18, and a blood return conduit 22 connected to a patient in a conventional manner such as via a catheter (not shown). The pump 16 may be a conventional pump, such as a roller pump.

The suction device 12 includes a tip portion 12a and a handle portion 12b. The blood aspirator 10 also includes a sensor 24 coupled to the tip portion 12a of the suction device 12 and a controller 30 connected to the sensor 24 via a signal line 32 and to the pump 16 via a signal line 34.

The controller 30 includes a microprocessor 40, a random-access memory (RAM) 42, a permanent memory in the form of a read-only memory (ROM) 44, and an input/output (I/O) circuit 46, all of which are interconnected via an address/data bus 48. The particular type of controller 30 used in not important to the invention. A display device 50 and an input device 52 may optionally be connected to the controller 30.

The controller 30 controls the speed of the pump 16 in response to the concentration of bubbles detected in the suction device 12. The sensor 24 may be an optical sensor that generates a beam of radiation (such as infrared radiation) that is passed through a transparent portion of the tip portion 12a and detects whether or not a bubble is present by detecting whether or not the radiation beam is interrupted, as sensed by a receiver portion of the sensor 24.

If the radiation beam is detected, then the sensor 24 generates a bubble-absent signal (e.g. a five-volt signal), whereas if no radiation beam is detected, the sensor 24 generates a bubble-present signal (e.g. a zero-volt signal).

In response to the concentration of bubbles detected in the suction device 12, the controller 30 adjusts the speed of the pump 16 by transmitting a drive signal to the pump 16 via the line 34. For example, the drive signal could be an analog drive signal that varies between zero and five volts, with a zero-volt signal corresponding to the lowest pump speed and a five-volt signal corresponding to the highest pump speed. Alternatively, the drive signal could be a multi-bit digital signal.

The manner in which the controller 30 controls the pump speed is described below in connection with FIG. 2, which is a flowchart of a main operating routine 100 stored in the ROM 44 and executed by the microprocessor 40. The main routine 100 is continuously performed while the blood aspirator 10 is in use.

Figure 2:
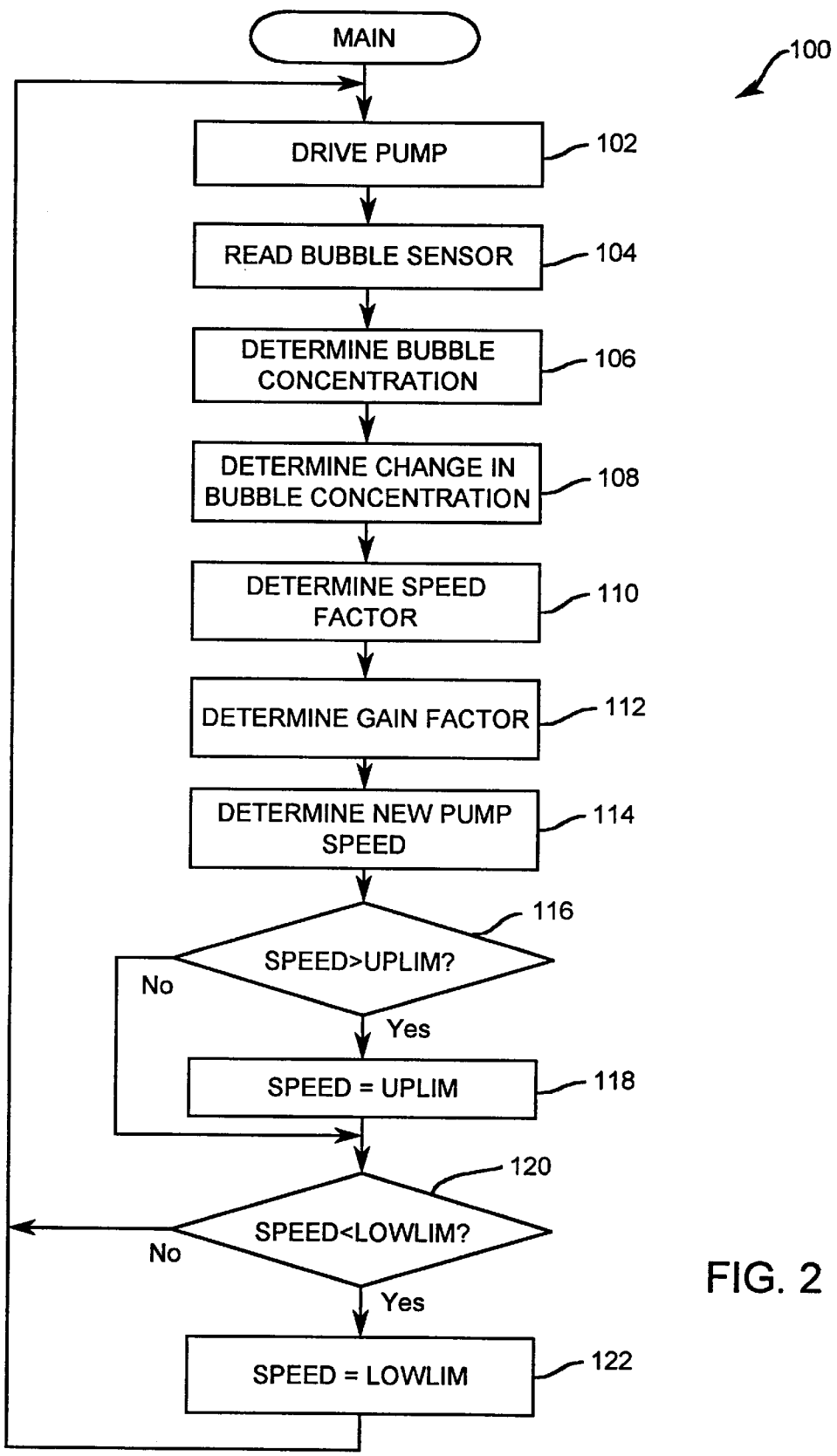
FIG. 2 is a flowchart of a main operating routine performed by the blood aspirator.

Referring to FIG. 2, at step 102, a drive signal is transmitted to the pump 16 via the line 34 to adjust the speed of the pump 16. When the blood aspirator 10 is first being used, the drive signal may be a predetermined signal that corresponds to a minimum level of pump speed or suction, such as 125 milliliters per minute. During subsequent performance of step 102, the magnitude of the drive signal is based on the bubble concentration, as described in more detail below.

At step 104, the sensor 24 is read or sampled a relatively large number of times, such as in excess of 1,000, during a predetermined period of time, such as 1.5 seconds, referred to herein as a sampling window. During such sampling window, the sensor 24 will typically generate a plurality of bubble-present signals and a plurality of bubble-absent signals. The total number of such signals will be the same as the number of times the sensor 24 was sampled.

If a sampling window is used and where the pump 16 is a roller pump, the duration of the sampling window is selected to be relatively long so that any flow variations due to the use of the roller pump are averaged out.

At step 106, the concentration of bubbles in the aspirated blood flowing through the suction device 12 is determined by dividing the number of bubble-present signals generated by the sensor 24 by the number of times the sensor 24 was sampled. For example, where the sensor 24 was sampled 10,000 times during the sampling window and where it generated 800 bubble-present signals, the bubble concentration determined at step 106 would be 8%.

At step 108, the change in bubble concentration is determined by calculating the difference between the bubble concentration just determined at step 106 and the bubble concentration determined during the previous performance of step 106. For example, if the bubble concentration just determined at step 106 is 8% and the previous bubble concentration determined at step 106 is 5%, the change in bubble concentration is 3%.

At step 110, a speed factor is determined based upon the bubble concentration determined at step 106 and the change in bubble concentration determined at step 108. Referring to FIG. 3, the speed factor is retrieved from a speed factor table stored in the memory (e.g. the ROM 44) of the controller 30. The speed factor table is in the form of a two-dimensional array of numeric values (each numeric value being represented by a two-letter acronym such as "PS"), each column of the array corresponding to a particular bubble concentration and each row of the array corresponding to a particular change in bubble concentration. The table of FIG. 3 has seven possible bubble concentrations (1%, 2%, 3%, 5%, 10%, 14% and 18%) and seven possible changes in bubble concentration (6%, 4%, 2%, 0%, −2%, −4%, −6%). The two letter acronyms of the speed factor table and their meanings and corresponding numeric values are set forth below:

| Acronym | Meaning | Value |
|---------|---------|-------|
| PL | Positive Large | .075 |
| PM | Positive Medium | .050 |
| PS | Positive Small | .025 |
| ZE | Zero | 0 |
| NX | Negative Small | −.025 |
| NM | Negative Medium | −.050 |
| NL | Negative Large | −.075 |

A positive speed factor, such as 0.075, will cause the magnitude of the pump drive signal on the line 34 to increase, and will therefore cause the pump speed to increase, with an increased rate of suction. A negative speed factor will cause the magnitude of the drive signal to decrease, causing the pump speed to decrease. The numeric values set forth above may correspond to predetermined increments of flow. For example, a speed factor of 0.025 may correspond to a change in flow of 16 milliliters per minute.

The above numeric values are selected to attempt to control the concentration of bubbles within the aspirated blood to 5% at all times. For example, if the bubble concentration is 5% and there is no change in the bubble concentration from the previous bubble concentration, the corresponding speed factor (at the intersection of the "0" row and "5" column) is ZE, which has a corresponding numeric value of zero. If the bubble concentration is 10% and the change in the bubble concentration from the previous bubble concentration is 2%, the corresponding speed factor (at the intersection of the "2" row and "10" column) is NS, which has a corresponding numeric value of −0.025, which will cause the suction rate to be decreased.

Controlling the bubble concentration to a relatively small, nonzero value is desirable in that a relatively high degree of suction can be maintained, while at the same time preventing the bubble concentration from increasing enough to cause significant blood damage. A relatively high degree of suction is desirable to keep the surgical area dry, or free of relatively large amounts of accumulated blood.

Since bubbles would not be generated if the end of the suction tip 12a were totally submerged in a pool of blood, the presence of some bubbles is desirable since it indicates that at least a portion of the end of the suction tip 12a is not submerged. Thus, the presence of some bubbles indicates that there is not a large pool of blood which needs to be evacuated (assuming that the suction tip 12a is being used properly by placing the end of the tip 12a at the bottom of the surgical area where blood is accumulating).

If the bubble concentration and change in bubble concentration do not exactly correspond to the numeric values used in the table, various approaches could be used to determine a speed factor. For example, if the bubble concentration was 4% and the change in bubble concentration was 1%, a weighted average of the speed factors could be used. In this case, the speed factor would be determined in accordance with the following equation:

$$\text{Speed Factor} = (\tfrac{1}{2}ZE + \tfrac{1}{2}NS + \tfrac{1}{2}PS + \tfrac{1}{2}ZE)/2$$

Alternatively, the speed factor could be selected based upon the bubble concentration and change in bubble concentration set forth in the table that were the closest to the actual bubble concentration and the actual change in bubble concentration. For example, if the actual bubble concentration was 7% and the actual change in bubble concentration was 1.5%, the speed factor corresponding to the "2" row and the "5" column could be selected.

Another method of determining the speed factor which incorporates fuzzy logic could used. This fuzzy logic method is described below in connection with FIGS. 4 and 5. FIG. 4 illustrates a graph of bubble concentration versus percent level that conceptually illustrates the interpolation of an actual bubble concentration between the bubble concentrations of the speed factor table of FIG. 3. In FIG. 4, each bubble concentration in the speed factor table is provided with an associated triangle which is used for interpolation purposes. For example, if the actual bubble concentration is 9% as represented by a vertical line in FIG. 4, the vertical line would intersect the triangle (in solid lines) for the 10% concentration at the 80% level and the triangle (in dotted lines) for the 5% concentration at the 20% level.

FIG. 5 illustrates a graph, similar to that of FIG. 4, of change in bubble concentration versus percent level that conceptually illustrates the interpolation of an actual change in bubble concentration between the changes in bubble concentrations of the speed factor table of FIG. 3. If the actual change in bubble concentration was 1.4%, the vertical line shown in FIG. 5 would intersect the triangle for 0% (shown in solid lines) at 30% and would intersect the triangle for 2% (shown in dotted lines) at the 70% level.

To determine the speed factor in accordance with this method, the four speed factors in the speed factor table which correspond to the triangles in FIGS. 4 and 5 that were intersected by the two vertical lines are used. For the example set forth above (9% bubble concentration and 1.4% change in bubble concentration), these four speed factors are shown in a darkened box 109 in FIG. 3. Then, the two rows and two columns which intersect those four speed factors are assigned the level percentages determined in connection with FIGS. 4 and 5. For this example, row "2" of the speed factor table has been assigned a 70% percentage; row "0" of the table has been assigned a 30% percentage; column "5" of the table has been assigned a 20% percentage; and column "10" of the table has been assigned an 80% percentage.

Each speed factor in the box 109 is then multiplied by the smaller of the two percentages which are associated with that speed factor. For example, the upper left-hand speed factor NS in the box 109 would be multiplied by 20%, since the 20% percentage associated with the "5" column is less than the 70% percentage associated with the "2" row.

After each speed factor in the box 109 is multiplied by the smaller corresponding percentage, the resultant values are added together and divided by the sum of the percentages used. For this example, the resultant speed factor would be equal to (0.20NS+0.70NS+0.30NS+0.20ZE)/1.4 (1.4 is the sum of 0.20, 0.70, 0.30, and 0.20). Various other methods of determining the speed factor at step 110 could be used.

Figure 6A:
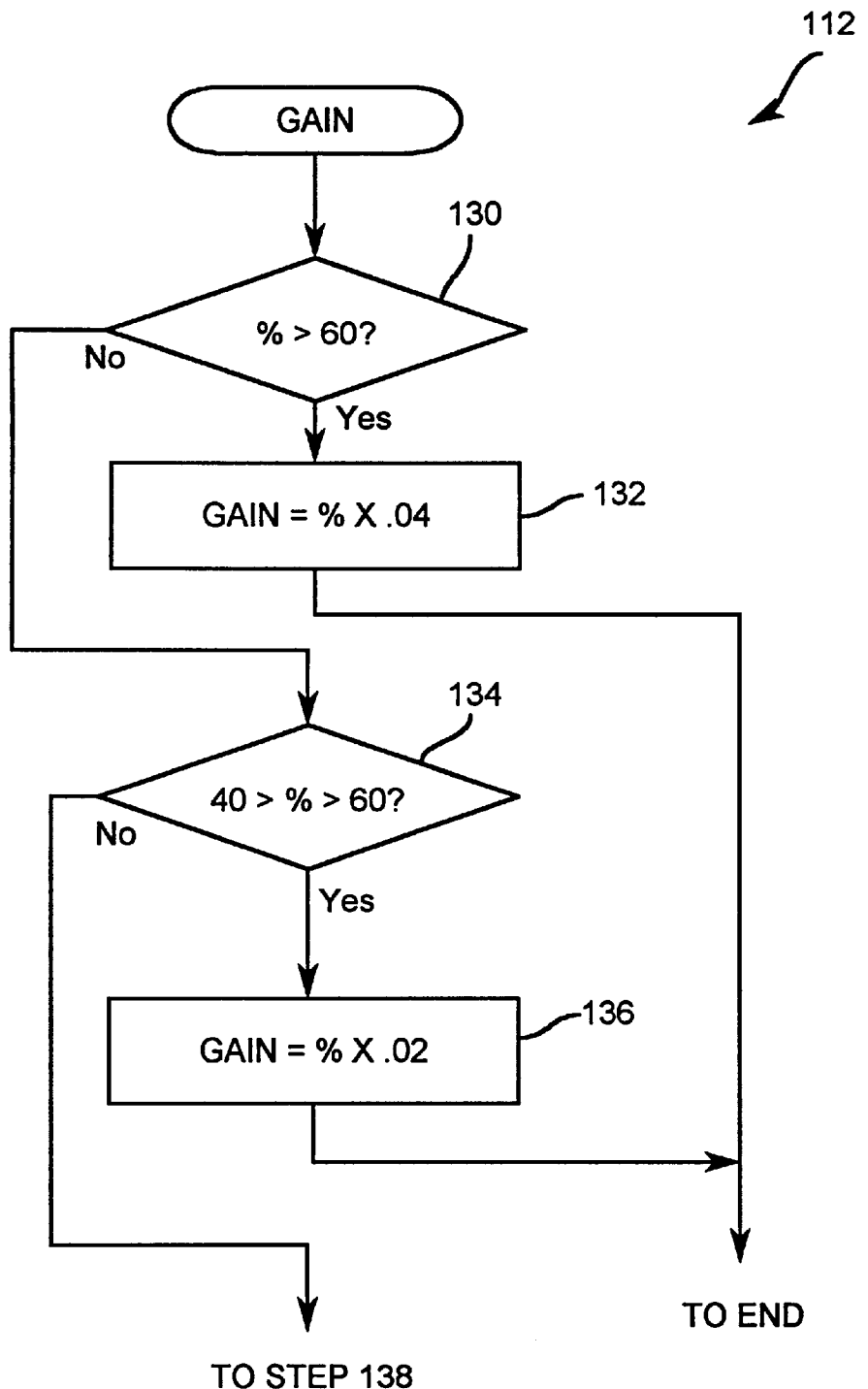
FIGS. 6A–6C illustrate a flowchart of a routine for determining a gain factor.
Figure 6B:
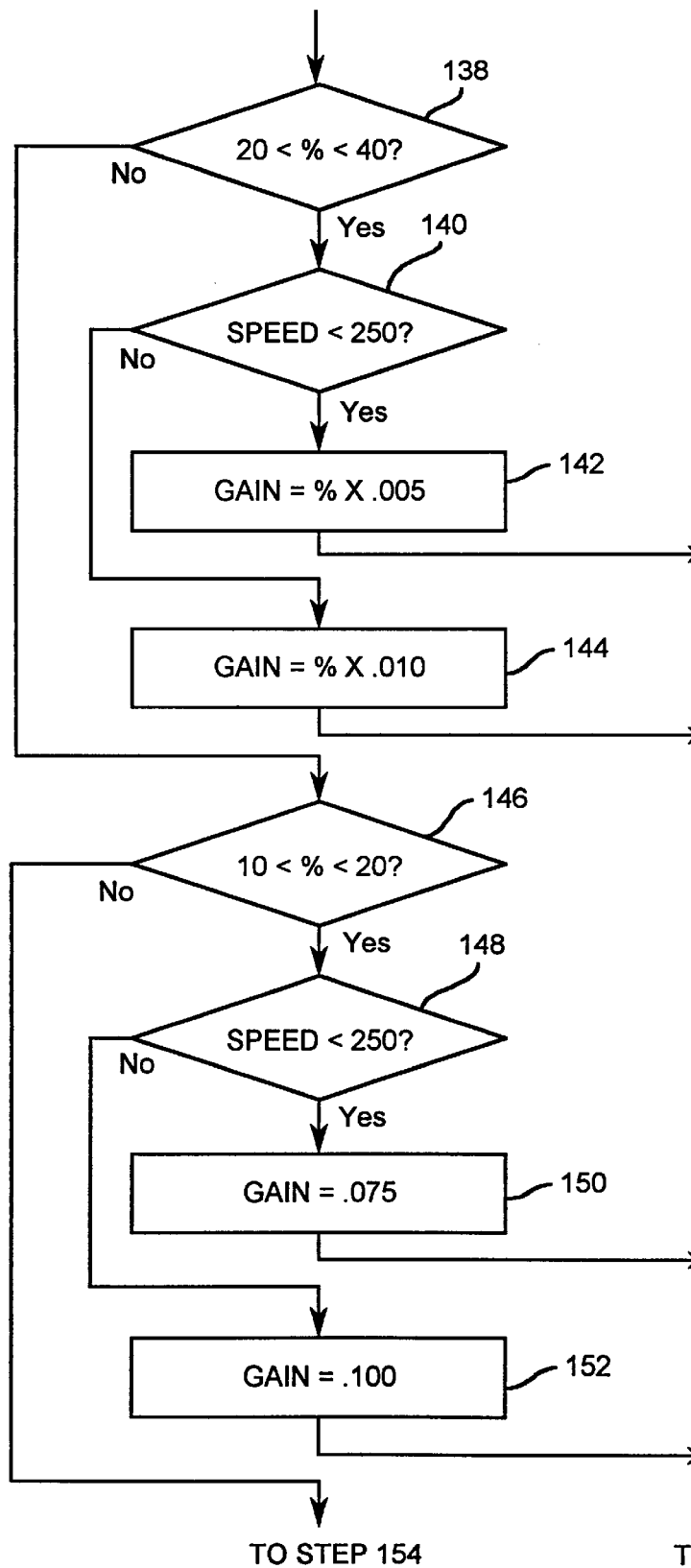
Figure 6C:
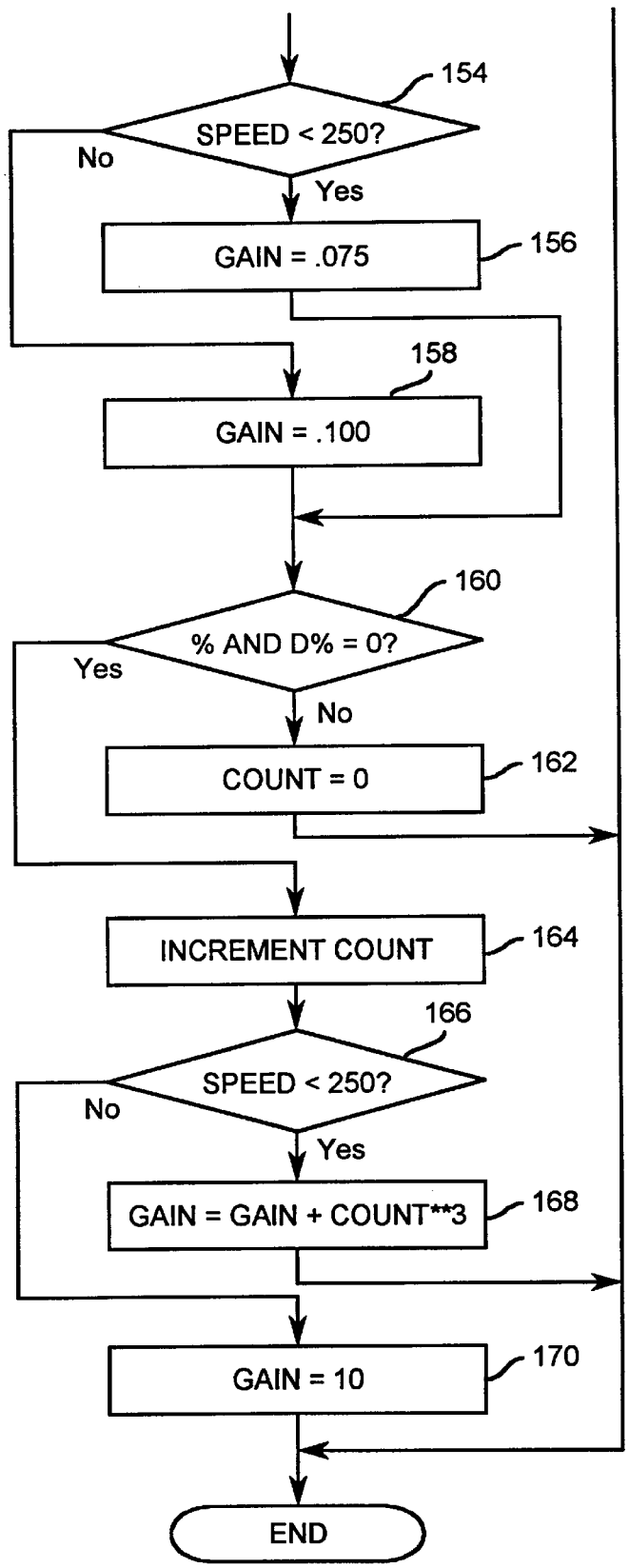

Referring back to FIG. 2, a gain factor is then determined at step 112. One example of how the gain factor could be determined is shown in FIGS. 6A–6C, which are a flowchart of a gain determination routine. A gain factor is assigned at step 112 based upon which of a plurality of predetermined bubble concentration ranges the actual bubble concentration falls within and the speed of the pump 16, which corresponds to the flow rate through the suction device 12 and the conduit 14.

Referring to FIG. 6A, at step 130, if the bubble concentration determined at step 106 (FIG. 2) is greater than 60%, the program branches to step 132 where the gain is set to 0.04 times the percentage bubble concentration (expressed as a whole number, not as a percentage). For example, if the bubble concentration was 70%, the gain would be set to 2.8. At step 134, if the bubble concentration determined at step 106 is between 40% and 60%, the program branches to step 136 where the gain is set to 0.02 times the percentage bubble concentration.

Referring to FIG. 6B, at step 138, if the bubble concentration determined at step 106 is between 20% and 40%, the program branches to step 140, where the current speed of the pump 16 is compared with a predetermined threshold value, such as 250 milliliters per minute. If the pump speed, and thus the flow through the suction circuit, is smaller than the threshold value, it is more likely that there is some statistical error in the bubble concentration determined at step 106 because a relatively low blood volume was inspected by the bubble sensor 24 (due to the relatively low blood flow). In this case, the sensitivity of the aspirator 10 is somewhat reduced by using a smaller gain value so that the aspirator 10 does not "overreact" to the bubble concentration. If the pump speed, and thus the blood flow, is greater than the threshold value, then a larger gain value is used.

At step 140, if the pump speed is less than the threshold value, the program branches to step 142 where the gain is set to 0.005 times the percentage bubble concentration. If the pump speed is not less than the threshold, the program branches to step 144 where the gain is set to 0.010 times the percentage bubble concentration.

At step 146, if the bubble concentration is between 10% and 20%, the program branches to step 148, where the pump speed is compared with the threshold value. If the pump speed is less than that value, the program branches to step 150 where the gain is set to 0.075. If not, the gain is set to 0.100 at step 152.

Referring to FIG. 6C, if step 154 is reached, then the bubble concentration is less than 10%. At step 154, if the pump speed is less than 250, the program branches to step 156 where the gain is set to 0.075. If not, the gain is set to 0.100 at step 158. At step 160, if the bubble concentration determined at step 106 and the change in bubble concentration determined at step 108 are not both zero, the program branches to step 162 where a count variable is set to zero. At step 160, if the bubble concentration and the change in bubble concentration are both zero, the program branches to step 164 where the count variable is incremented by one.

The count variable is used to measure any continuous period of time for which the aspirator 10 has detected no bubbles. This time corresponds to the duration for which the bubble concentration is zero and the rate of change of bubble concentration is zero. A significant time period for which no bubbles have been detected may correspond to a situation where blood has increased at the surgical area at a relatively large rate, due to the cutting of an artery, for example. In this case, it is desirable to increase the suction rate more quickly than usual if the suction rate is below a given threshold, such as 250 milliliters per minute.

At step 166, if the pump speed is less than 250, the program branches to step 168 where the gain is determined by adding the gain value determined at step 156 to the cube of the count determined at step 164. For example, if the current count is two, the gain value determined at step 168 would be 0.075+8, or 8.75. If the pump speed was not less than 250 as determined at step 166, then the gain is set equal to a predetermined value, such as 10.

The particular gain values, bubble percentage ranges, pump speed values, and threshold values shown in FIGS.

6A–6C are not considered important to the invention, and other values could be used.

Referring back to FIG. 2, at step 114 the new pump speed is determined based upon the current pump speed, the speed factor determined at step 110 and the gain factor determined at step 112, in accordance with the following equation:

New speed=current speed+(speed factor×gain factor)

As stated above, the pump speed may be represented by an analog value between zero and five volts (which is transmitted to the pump 16 via the line 34).

After the new speed is determined, at step 116 the new speed is compared to determine whether it is greater than a predetermined upper limit. The upper limit may be used for safety reasons to prevent the aspirator 10 from removing blood from a patient at very large rates, such as two liters per minute. If the new speed determined at step 116 is greater than the upper limit, the program branches to step 118 where the new speed is set equal to the numeric value of the upper limit.

At step 120 the new speed is compared to determine whether it is less than a predetermined lower limit. A lower speed limit may be used to guarantee that the aspirator 10 maintains a minimum suction rate so that the amount of blood sampled by the bubble sensor 24 is large enough to guarantee statistically significant data relating to the bubble concentration. At step 120, if the new speed is less than the predetermined lower limit, the program branches to step 122 where the new speed is set equal to the numeric value of the lower limit. The numeric values of the upper and lower limits may be selected to correspond to the desired upper and lower flow limits of the pump 16, such as a lower flow limit of 125 milliliters per minute and an upper flow limit of one liter per minute.

After the new pump speed is set at one of steps 114, 118, or 122, the program branches back to step 102 where the signal corresponding to the new pump speed is transmitted to the pump 16 via the line 34 to drive the pump 16 at its new speed. Steps 104–122 are continuously repeated while the aspirator 10 is in use to control the pump speed as described above.

The handle 12b of the suction device 12 could be provided with a switch to override the output of the bubble sensor 24, e.g. a switch that provided a predetermined voltage on the line 32, so that a continuous bubble-absent signal was generated. The purpose of the override switch would be to cause the aspirator 10 to increase the suction rate at its maximum rate of increase, which could be used, for example, where a surgeon was about to make an incision which would cause a large amount of bleeding.

Although the new pump speed is described above as being determined based upon a speed factor and a gain factor, it is not considered necessary to the invention that both factors be used to determine the new pump speed. For example, instead of separately determining a speed factor and a gain factor, a single speed adjustment factor could be used. Such a factor could be stored in a memory table which has numerous such factors, one of which is selected based upon the bubble concentration, the change in bubble concentration, and/or the current pump speed.

Instead of using values stored in a memory table to determine the new pump speed, the new speed could be determined in accordance with one or more equations which take into account the bubble concentration, the flow rate through the suction circuit, and/or the change in bubble concentration over time.

Although the sensor 24 is disclosed above as being an optical sensor, other types of sensors could be utilized. For example, a conventional impedance sensor for sensing the impedance at a point across the suction device could be used to generate the bubble-present and bubble-absent signals. Since air bubbles have a different impedance than blood, if a bubble was present, the impedance across the suction device 12 would be different than if a bubble were not present.

Instead of a sensor which detects whether or not one or more bubbles are present at a particular point, a sensor that generates a signal indicative of the bubble concentration along a length of the suction device could be used. For example, an impedance sensor in the form of a pair of impedance-sensing devices spaced along a length of the suction device 12 could be utilized to generate a signal indicative of the impedance between them, and thus indicative of the bubble concentration. In such case, step 106 of FIG. 2 would be unnecessary since the signal generated by such an impedance sensor would already be indicative of the bubble concentration.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A blood aspirator apparatus, comprising:

a suction circuit adapted to receive a flow of blood having a magnitude and a concentration of bubbles therein;

a sensor associated with said suction circuit that generates a plurality of bubble detection signals;

a variable speed pump coupled to said suction circuit and adapted to pump blood through said suction circuit at a variable rate; and a controller operatively coupled to said sensor and said variable speed pump, said controller generating a plurality of bubble concentration signals based upon said bubble detection signals, each of said bubble concentration signals being indicative of said concentration of bubbles, said controller generating a concentration change signal based upon at least two of said bubble concentration signals, said concentration change signal being indicative of a change in concentration of said bubbles between a first time and a second time, and said controller generating a flow signal indicative of said magnitude of blood flow through said suction circuit, said controller controlling said variable speed pump based upon said bubble concentration signal, said concentration change signal and said flow signal, said controller causing said variable speed pump to increase said blood flow through said suction circuit when said bubble concentration is lower than a predetermined nonzero value, and said controller causing said variable speed pump to decrease said blood flow through said suction circuit when said bubble concentration is higher than a predetermined nonzero value.

2. A blood aspirator apparatus as defined in claim 1 additionally comprising a memory which stores a plurality of bubble concentration ranges, each of said ranges having an associated factor relating to a speed of said variable speed pump, wherein said controller determines which of said bubble concentration ranges said bubble concentration falls within and controls the speed of said variable speed pump based upon said speed factor associated with said determined bubble concentration range.

3. A blood aspirator apparatus as defined in claim 1 wherein said suction circuit comprises a blood suction device and a conduit fluidly connected to said blood suction device.

4. A blood aspirator apparatus as defined in claim 3 wherein said blood suction device comprises a tip portion and wherein said sensor is disposed adjacent said tip portion.

5. A blood aspirator apparatus as defined in claim 1 wherein said sensor comprises generates one of said bubble detection signals each time a bubble is detected.

6. A blood aspirator apparatus as defined in claim 1 wherein said sensor comprises an optical sensor that detects whether or not a radiation beam passing through said suction circuit is interrupted by a bubble.

7. A blood aspirator apparatus as defined in claim 1 wherein said sensor is periodically sampled at a predetermined rate over a period of time, said sensor generating either a bubble-present signal or a bubble-absent signal each time said sensor is sampled, and wherein said controller determines the number of bubble-present signals that are generated during said period of time and divides said number of bubble-present signals by the number of times said sensor is sampled during said period of time.

8. A blood aspirator apparatus as defined in claim 1 wherein said controller generates a pump drive signal which determines the rate at which said variable speed pump operates.

9. A blood aspirator apparatus, comprising:
   a suction circuit adapted to receive a flow of blood having a magnitude and a number of bubbles therein;
   a sensor associated with said suction circuit which generates a signal relating to the presence of bubbles in said suction circuit;
   a variable speed pump coupled to said suction circuit and adapted to pump blood through said suction circuit at a variable rate; and
   a controller operatively coupled to control said variable speed pump, said controller causing said variable speed pump to increase said blood flow through said suction circuit when bubbles are present as determined by said sensor.

10. A blood aspirator apparatus as defined in claim 9 wherein said controller causes said variable speed pump to adjust said blood flow through said suction circuit so that a nonzero concentration of bubbles flows through said suction circuit.

11. A blood aspirator apparatus as defined in claim 9 wherein said controller causes said variable speed pump to increase said blood flow through said suction circuit in response to a bubble concentration that is lower than a predetermined nonzero value and wherein said controller causes said variable speed pump to decrease said blood flow through said suction circuit in response to a bubble concentration that is higher than a predetermined nonzero value.

12. A blood aspirator apparatus as defined in claim 9 wherein said suction circuit comprises a blood suction device and a conduit fluidly connected to said blood suction device.

13. A blood aspirator apparatus as defined in claim 12 wherein said blood suction device comprises a tip portion and wherein said sensor is disposed adjacent said tip portion.

14. A blood aspirator apparatus as defined in claim 9 wherein said bubbles in said suction circuit have a concentration and wherein said blood suction apparatus additionally comprises a memory which stores a plurality of bubble concentration ranges, each of said ranges having an associated factor relating to a speed of said variable speed pump and wherein said controller determines which of said bubble concentration ranges said bubble concentration falls within and controls the speed of said variable speed pump based upon said speed factor associated with said determined bubble concentration range.

15. A blood aspirator apparatus, comprising:
   a suction circuit adapted to receive a flow of blood having a magnitude and a concentration of bubbles therein;
   a sensor associated with said suction circuit that generates a signal relating to the concentration of bubbles in said suction circuit;
   a variable speed pump coupled to said suction circuit and adapted to pump blood through said suction circuit at a variable rate; and
   a controller that controls said variable speed pump based upon said signal relating to the concentration of bubbles in said suction circuit and a flow signal representing the magnitude of blood flow through said suction circuit.

16. A blood aspirator apparatus as defined in claim 15 wherein said controller controls said variable speed pump additionally based on the rate of change over time of said bubble concentration.

17. A blood aspirator apparatus as defined in claim 15 additionally comprising a memory that stores a plurality of bubble concentration ranges, each of said ranges having an associated factor relating to a speed of said variable speed pump, and wherein said controller determines which of said bubble concentration ranges said bubble concentration falls within and controls the speed of said variable speed pump based upon said speed factor associated with said determined bubble concentration range.

18. A blood aspirator apparatus as defined in claim 15 wherein said suction circuit comprises a blood suction device and a conduit fluidly connected to said blood suction device.

19. A blood aspirator apparatus as defined in claim 18 wherein said blood suction device comprises a tip portion and wherein said sensor is disposed adjacent said tip portion.

20. A blood aspirator apparatus as defined in claim 15 wherein said sensor generates a bubble detection signal each time a bubble is detected.

* * * * *